United States Patent [19]

Weber et al.

[11] 4,368,270
[45] Jan. 11, 1983

[54] PROCESS FOR THE RECOVERY OF ENZYME COAGULANTS

[75] Inventors: Meyer M. Weber, Milwaukee; John Shovers, Shorewood, both of Wis.

[73] Assignee: Midwest Biochemical Corp., Milwaukee, Wis.

[21] Appl. No.: 322,010

[22] Filed: Nov. 16, 1981

Related U.S. Application Data

[63] Continuation of Ser. No. 124,099, Feb. 25, 1980, abandoned.

[51] Int. Cl.$^3$ .............................................. C12N 9/64
[52] U.S. Cl. .................................................. 435/226
[58] Field of Search ................................ 435/226, 816

[56] References Cited

U.S. PATENT DOCUMENTS 2,567,378  9/1951  Kennedy et al. ................... 435/226
2,701,228  2/1955  McKerns ............................. 435/226
3,660,237  5/1972  Schultz ................................ 435/226

Primary Examiner—Lionel M. Shapiro
Attorney, Agent, or Firm—Andrus, Sceales, Starke & Sawall

[57] ABSTRACT

A process for improving the recovery of enzyme coagulants from animal organs comprising the steps of adding a polar solvent having a surface tension in the range of about 18 to 72 dyne.cm$^{-1}$ to the finely divided organs and thereafter adding salt solution to the organ/polar solvent mixture to extract the enzyme coagulants. Subsequently, the extract is activated by lowering the pH to a value in the range of 3.2 to 4.8 and gel-like substances such as mucin, are removed. The process results in an improved enzyme yield and minimizes the loss of enzyme activity to improve the stability.

12 Claims, No Drawings

PROCESS FOR THE RECOVERY OF ENZYME COAGULANTS

This is a continuation of application Ser. No. 06/124,099, filed Feb. 25, 1980, now abandoned.

BACKGROUND OF THE INVENTION

Enzyme coagulants such as rennin and pepsin are used extensively as milk coagulants in cheesemaking.

Rennin is formed from the inactive precursor, prorennin. The process, which has not been investigated in detail, is quite rapid below a pH of 3.0. Whether enzymatic activation by rennin itself occurs has not been established with certainty, although there is some indication that the process is autocatalytic. The molecular weight of rennin is about 40,000, and the enzyme has been obtained in crystalline form. The isoelectric point is about 4.5, which is considerably higher than that of pepsin. The pH optimum for activity of the enzyme with hemoglobin is 3.7 and its maximum stability in solution is near a pH of 5.5 to 5.8.

The enzyme, which has many similarities to pepsin is present in the lining of the fourth stomach of the calf. It is important to distinguish between the enzyme rennin and the extracts which are produced from the stomachs of calves, young lambs, or young goats. Rennin is the proteolytic agent of milk clotting found in rennet, but other enzymes may be present in the crude commercial extracts. If the enzyme is obtained from the stomach of calves which have been fed anything but milk, it will be contaminated with pepsin.

Although rennet is the preferred enzyme, other animal enzymes present in animal organs, such as stomachs, can be extracted and are useful for coagulating. For example, the enzyme pepsin comprises about 10% of the active coagulant found in veal organs, about 65% of the active coagulant in bovine organs and up to 100% of the active coagulant found in hog organs. Thus, it can be appreciated, the commercial extracts of animal coagulants will vary in the amount of enzymes present at a standard level of coagulating activity. Thus, the term enzyme coagulants is used in the description of the present invention.

Listed in Table I below are typical assays of various animal coagulants and their usage rates relative to standardized rennet which was assigned a usage factor of 1.00. Usage factors of other animal coagulants are based on the ratio of 12% reconstituted powdered milk/whole milk of the sample to the 12% reconstituted powdered milk/whole milk of the rennet standard. The % of Active Rennet (A.R.) describes the relative activity of each sample compared to that of the rennet standard in whole milk at a pH of 6.5. Thus, the theoretical 12% reconstituted powdered milk/whole milk coagulating units (RU) for a sample can be established to obtain equivalent activity in the cheese vat to rennet.

TABLE I

| Sample | Reconstituted Dry Milk(12%) at pH 6.3 RU/ml | Whole Milk at pH 6.5 RU/ml | Reconstituted Dry Milk/ Whole Milk | Usage Factor | % of A.R. Equivalent Activity |
|---|---|---|---|---|---|
| Standard Veal | 100 | 31.6 | 3.16 | 1.00 | 100 |
| Standard Bovine | 242 | 30.6 | 7.91 | 2.67 | 97 |
| Standard Bovine | 236 | 35.0 | 6.75 | 2.15 | 111 |
| Fungal - Type A | 168 | 32.4 | 5.18 | 1.65 | 99 |
| Fungal - Type B | 124 | 33.5 | 3.70 | 1.16 | 104 |
| 50% Veal/50% Bovine | 260 | 63.2 | 4.10 | 1.34 | 192 |
| 50% Veal/50% Bovine | 310 | 71.2 | 4.35 | 1.40 | 219 |

When rennet is obtained from the fourth stomach of young calves, either fresh or dried strips of the mucosa cut from the stomach are used. One method of preparing rennin in powder form is to mince the mucosa, adjust to pH 2.0 to 3.0 with hydrochloric acid, and incubate the thin slurry at 42° C. (108° F.) to convert the zymogen, prorennin, to rennin. The pH is next adjusted to 5.5 with sodium phosphate, and the whole fluid mass dried in a vacuum and powdered. Fat may be removed from the dry powder by solvent extraction.

Another method of preparing rennin comprises stirring for several days at pH 5.2, the dried and ground, or the minced tissue with 5% to 10% sodium chloride solution containing 2% to 4% of boric acid or other preservative. The extract is strained from the undissolved tissue, acidified with hydrochloric acid to ph 2.5, and allowed to stand for about 3 days. This activates the prorennin and coagulates mucin and other colloidal matter. The extract, after adjustment to pH 5.3 to 6.3, wherein rennin is most stable, is clarified by filtration. It may be evaporated at low temperature under vacuum and is marketed as a single, double, or triple strength rennet extract. A powder is obtained by precipitating with excess sodium chloride or sodium sulfate at the isoelectric point, pH 3.6, and allowing it to stand for 12 hours, filtering and drying. It is sold as standardized rennet powder.

Liquid rennet preparations generally have a pH between 5.6 and 5.8 in order to provide the most stable environment. The rennet extract can be sterilized by filtration through filters which retain bacteria, and other methods of sterilization by acids, iodine, or by heating have been suggested. Rennet contains considerable amount of pepsin if stomachs of older calves or cows are included with the stomachs of suckling calves. If the calves are fed anything else but milk, the stomach extracts will also contain pepsin. In many countries the stomachs of sheep and goats (or lambs and kids) are used. Extraction of such stomachs can be carried out with 10% acetic acid solutions by treating 100 g of the stomach with 500 ml of the acid five times at 30° C. and during a 24 hour period. The extracts are combined, filtered, and vacuum concentrated to 20 ml.

The commercial extraction of rennet heretofore included washing and drying the rennet for 3 to 6 days and grinding the rennet with cellulosic fiber, such as excelsior, wood chips, for up to a day and one-half, adding water and countercurrent extracting for 2 to 6 days. These steps are repeated until the standardized strength is obtained. The residue had little utility due to the presence of wood chips, etc. Some methods today use reverse osmosis to concentrate the extract followed by an ultrafiltration step.

Most commercial processes presently on stream subject the various enzyme coagulants to hostile conditions relative to stability. For example, various air drying procedures used to dewater animal organs, prolonged counter current extractions, although somewhat effective in achieving release of these enzyme coagulant from the animal organs, create hostile conditions for these sensitive enzyme coagulants. The result is that reductions in yield are attributed in part to loss of enzyme coagulants due to instability.

It has been found that air drying of rennets results in loss of activity as shown in Table II below.

TABLE II

AIR DRIED - vs - VACUUM DRIED - vs - UNDRIED RENNET FOR EXTRACTION

| Treatment | % Activity | % Recovery |
|---|---|---|
| Rennets Dried 1½ days in air drier. Ground in hammer mill and extracted overnight at pH 6.0 | 38.5 | 87.5 |
| Same lot of rennets dried in vacuum drier for 24 hours. Ground and extracted as above. | 45.5 | 100.00 |
| Same lot of rennets-ground in meat grinder to a fine grind. Extracted as above. | 45.5 | 100.00 |

It has been observed that certain pre-treatments of the animal organs prior to extraction have no noticeable effect on activity. For example, grinding the organs to various mesh sizes does not appear to affect the activity level, provided the organs are fresh or frozen and not allowed to stand at room temperature for prolonged periods. This is shown in Table III below.

TABLE III

| Type of Animal Organ | Type of Grinder Used | % Activity at 16 Hrs. |
|---|---|---|
| Bovine Stomach (Source A) | Meat Grinder fitted with ⅛" head | 58 |
| Bovine Stomach (Source A) | Meat Grinder fitted with 1/16" head | 60 |
| Bovine Stomach (Source B) | Meat Grinder fitted with ⅛" head | 38 |
| Bovine Stomach (Source B) | Meat Grinder fitted with 1/16" head | 40 |

SUMMARY OF THE INVENTION

The present invention is directed to a process for recovering enzyme coagulants from animal organs that minimizes loss of enzyme activity, improves yield, and process time, and provides a residue that is usable as animal feed.

In accordance with the process of the invention, the ground or chopped animal organs are initially mixed with a polar solvent having a surface tension in the range of 18 to 72 dyne.cm$^{-1}$, and thereafter the organ/polar solvent mixture is extracted in an aqueous salt solution having a pH of about 5.8 to 6.0 to extract the enzyme coagulants. Subsequently, the pH of the extract is lowered to a value of about 3.2 to 4.6 to activate the enzymes.

To dehydrate and remove the gel-like substances, such as mucin, from the extract, a soluble salt, such as aluminum sulfate, which is capable of reacting with the mucin present in the organ at a pH of about 3.4, is added to the extract followed by the addition of a precipitating salt, such as sodium phosphate, that is reactive with the soluble salt/mucin complex, precipitating the soluble salt at a pH of about 5.6 to 6.0. The organs in the extract are then dewatered by use of a mechanical press, and the extract is then filtered to remove the precipitate and mucin and concentrated to standard activity.

The advantages of the process of the present invention are two-fold. The total enzyme coagulant recovered is increased dramatically and the process conditions of the invention favor less loss of enzyme coagulant due to instability.

The process of the present invention requires a cycle time from between about 24 and about 38 hours for a 2,000 gallon charge; using typical batch processing techniques. In contrast, typical counter current extraction processes employed today require a minimum of 120 hours to complete. This additional exposure of the enzyme coagulant held under dilute conditions at temperatures ranging from about 40° F. to 65° F., is believed to be a major factor influencing recovery yields.

DESCRIPTION OF THE PREFERRED EMBODIMENT

A specific illustration of the process of the invention is shown in the following Table IV:

TABLE IV

| General Step | Specific Process Steps | Time Required in Hours |
|---|---|---|
| Prepare animal organ for extraction | Grind raw Bovine stomachs, add polar solvent | 1 |
| Extraction | Add 5% NaCl solution. Adjust pH to 5.8 to 6.0. Agitate | 4 |
| Activation | Adjust pH to 3.2 to 4.8 by addition of acid | 2 to 14 |
| Add soluble salt and precipitate salt/ mucin complex | Add Al$_2$(SO$_4$)$_3$(0.5 to 1.0%) to pH 3.4. Follow with addition of Na$_3$(PO$_4$)$_2$ to pH 5.6 to 6.0 | 1 1 |
| Add filter aid and dewater organs | Add 1% diatomaceous earth and dewater organs by conventional press | 3 |
| Filter extract | Add 3% diatomaceous earth and filter extract through conventional filter press | 4 |
| Concentrate Extract | Reverse osmosis used to concentrate to standard activity | 6 |
| Standardized Package | Add salts and preservatives | — |

The animal organs that are ground and mixed with the polar solvent can be stored for prolonged periods at cool temperatures, such as 32° F. to 40° F. before processing. Surprisingly, it has been found that the enzyme coagulants present remain stable for prolonged periods and in fact total enzyme coagulant recovery yields showed improvement when the mixture was allowed to stand for up to 48 hours prior to processing. This is set out in table V below:

TABLE V

| ADDITIVE % by Weight | Step In Process When Additive Is Introduced | Total Process Time in Hours | Results in Stomachs per gal of finished standardized enzyme coagulant solution |
|---|---|---|---|
| 5% NaCl mucin modification | Extraction | Approx. 24-36 | 14 to 15 |
| Polar Solvent(propylene glycol) (No NaCl added in extraction step) | At time grinding | Approx. 24-36 | 12 to 14 |
| 5% NaCl plus 10% polar solvent (propylene glycol) | Solvent added 48 hrs. prior to extraction - stomach held at 32-40° F., NaCl added in extraction | Approx. 24-36 | 9 to 10 |
| 5% NaCl plus 10% polar solvent (propylene glycol) | Solvent added 24 hours prior to extraction - stomach held at 32-40° F., NaCl added in extraction | Approx. 24-36 | 10 to 11 |
| 5% NaCl plus 10% polar solvent (propylene glycol) | Solvent added just prior to extraction | Approx. 24-36 | 10 to 13 |

It appears the polar solvent penetrates the animal organ and has unique affinity to the enzyme coagulant and capacity to aid in the stabilizing of the enzyme coagulant. The combination of the polar solvent and the salt solution present during the extraction step has a synergistic effect, resulting in an increased yield of enzyme coagulant from the animal organ, as well as a more stable enzyme coagulant present in the mother liquor. Additionally, the extraction step in the present invention requires approximately 4 hours using agitation at a pH of from between about 5.8 and 6.0. This is in contrast to the countercurrent extraction techniques used in the former processes which required 72 to 120 hours using vats in tandem.

The activation step which converts the enzyme coagulant precursors into the enzyme per se can be accomplished in a rapid manner by adjusting the pH to 3.2, or it can be achieved in a longer period of time at a higher pH of about 4.6. In either case, the pH adjusting is carried out with the addition of an acid such as hydrochloric acid. The slower activation process is preferred for optimum yield. The time for activation generally is from between 2 to 16 hours.

In order to maximize the recovery of the enzyme coagulant retained in the animal organ it is imperative that the organ be dewatered under conditions which are not hostile to the stability of the enzyme coagulant. Often the organs contain substances, such as mucin, which are gel-like materials that interfere with the removal of water and coagulant. Resorting to harsh deatering processes, such as air drying or prolonged countercurrent extraction processes, lowers the enzyme recovery.

The modification of mucin prior to dewatering is achieved by the addition of a soluble salt that is reactive with mucin at a pH of about 3.4, followed by the precipitation of the salt at a pH from about 5.8 to about 6.0 with a precipitating salt that is reactive with the salt/mucin complex. The net effect of the sequential salt addition and precipitation is that the mucin is physically modified. The animal organs present are then capable of being dewatered. The mother liquor contains the enzyme coagulant, the soluble ions of the various salts used in the process and the polar solvent.

The polar solvent added to the animal organ prior to extraction in the process of the invention has an affinity for the enzyme coagulant present in the organ and has a stabilizing influence on enzyme coagulant. The surface tension of suitable polar solvents is generally from between about 18 and about 72 dyne.cm$^{-1}$. Examples of suitable polar solvents and their surface tension values are shown in Table VI below:

TABLE VI

| SUBSTRACT | TEMP °C. | SURFACE TENSION dyne.cm$^{-1}$ a | b |
|---|---|---|---|
| Acetone | 20 | 26.26 | 0.112 |
| Acetamide | 110 | 47.66 | 0.1021 |
| Acrylonitrile | 20 | 29.58 | 0.1178 |
| 1,3 Butanediol | 20 | (37.8 at 25° C.) | |
| Diethyl ether | 15 | 18.92 | 0.0908 |
| 1,2-Ethanediol | 15 | 50.21 | 0.0890 |
| Ethanol | 25 | 24.05 | 0.0832 |
| Furan | 20 | (24.10 at 20° C.) | (23.38 at 25° C.) |
| Glycerol | 25 | (63.14 at 17° C.) | (62.5 at 25° C.) |
| Isopropyl acetate | 20 | 24.44 | 0.1072 |
| 1,2 Propanediol | 20 | (72.0 at 25° C.) | |
| Pyrrole | 20 | 38.81 | 0.1100 |

The concentration of the polar solvent used can cover a broad range depending on the polarity/surface tension of the solvent and its ability to penetrate the organ and its affinity for the enzyme coagulant. It is preferred to use a concentration of polar solvent from between about 1 and about 10% by weight. Particularly preferred is a concentration from between about 5% and about 15% by weight where the solvent has a surface tension of about 72 dyne. cm$^{-1}$ at 20° C., such as 1,2-propanediol(propylene glycol).

The salt solution, which can be a solution of sodium chloride or sodium sulfate, in combination with the polar solvent improves the yield of the enzyme coagulant as well as the stability thereof. Furthermore, the polar solvent/salt solution mixture has a synergistic effect on enzyme coagulant recovery in that it allows the recovery to be accomplished in a shorter time frame.

The influence of sodium chloride concentration on enzyme coagulant activity in the process of the invention is described in Table VII below. It is believed that there is a critical concentration balance of polar solvent and sodium chloride to obtain optimum results.

TABLE VII

| % NaCl In Slurry | % Activity |
|---|---|
| 0.0 | 49.5 |

TABLE VII-continued

| % NaCl In Slurry | % Activity |
|---|---|
| 2.0 | 50.2 |
| 5.0 | 54.3 |
| 10.0 | 47.4 |

It is necessary to effectively dewater the organs under conditions most favorable to enzyme coagulant stability and the most favorable conditions are at a pH of about 3.4. Most organs contain substances that have an affinity for the enzyme coagulant and water. Typically, these substances are gel-like, such as mucin. They tend to interfere with water removal and trap substantial quantities of enzyme coagulant.

In the process of the invention, the mucin is modified physically and rendered innocuous by the addition of selected soluble salts to the extract, while maintaining the pH at about 3.4. It is believed that the addition of the soluble salt dehydrates or modifies the structure of the mucin, destroying its ability to hold water. The addition of the soluble salt is followed immediately by the addition of a precipitating agent that precipitates the soluble salt from the extract at a pH from between about 5.8 and 6.0.

The preferred soluble salts include aluminum salts, such as $Al_2(SO_4)_3$, $AlCl_3$, $KAl\ SO_4$, alum and mixtures thereof. These salts in concentrations from between about 0.5% to about 1.0% by weight are preferred.

The preferred precipitating agent contains an alkaline precipitating cation characteristic of phosphates, hydroxides and oxides. Specifically, substances such as $Na_3(PO_4)_2$, $K_3(PO_4)_2$ $CaO$, $KOH$, and $NaOH$ are preferred.

The precipitating substances are added at concentrations sufficient to neutralize the soluble salt/mucin complex present. Generally, these are present in concentrations ranging from about equal to about 50% greater than the concentration of the soluble salt.

The effect of various aluminum salts on activity in the filtrate are shown in Table VIII below:

TABLE VIII

EFFECT OF VARIOUS ALUMINUM SALTS

| Salt | % Needed To Adjust From pH 4.6 to 3.3. | % Activity In Filtrate |
|---|---|---|
| $Al_2(SO_4)_3$ | 1.0 | 33.0 |
| $Al\ Cl_3$ | 0.4 | 34.0 |
| $KAl\ SO_4$ | 1.1 | 35.5 |
| Alum | 1.2 | 36.3 |

The effect of $Al_2(SO_4)_3$ concentration on filtrate clarity is shown in Table IX below:

TABLE IX

| % Used | pH After Addition | mls. satd. $Na_3PO_4$ to adjust to 5.8 | mls. filtrate obtain in 10 mins. from 100 initial | Clarity |
|---|---|---|---|---|
| 0.25 | 3.8 | 1.2 | 34 | Fair |
| 0.5 | 3.5 | 1.7 | 31 | Good |
| 1.0 | 3.3 | 3.0 | 27 | Good |

The optimum pH range for the rennet extract recovery using $Al_2(SO_4)_3$ precipitation is shown in Table X below:

TABLE X

| pH Value | Times Concentrated | Activity | % Recovery |
|---|---|---|---|
| 5.2 | 2.0 | 59 | 99 |
| 5.4 | 2.4 | 70 | 100 |
| 5.6 | 2.0 | 58 | 98 |
| 5.8 | 2.0 | 55 | 90 |
| 6.0 | 2.8 | 75 | 87 |

The influence of $Al_2(SO_4)_3$ salt on high temperature stability of rennet is shown in Table XI below:

TABLE XI

| Treatment | % Activity Remaining After Being Held At 50° C. for 15 minutes |
|---|---|
| Unheated Control | 100.0 |
| Heated Control | 90.0 |
| 0.01% $Al_2(SO_4)_3$ added | 93.0 |
| 0.05% $Al_2(SO_4)_3$ added | 96.0 |
| 0.10% $Al_2(SO_3)_4$ added | 97.0 |

The apparent increase in high temperature stability is achieved by the addition of low concentrations of $Al_2(SO_4)_3$. The data suggests that the long term shelf stability might also be increased.

After the organs have been treated to render them suitable for dewatering, various filtering aids such as diatomaceous earth, ground lava rock, bentonite, asbestos, etc. can be added at concentrations from between about 1 and about 3% by weight. Traditional dewatering, filtering, concentrating and standardizing procedures are followed including the use of conventional filter presses, vacuum concentration, reverse osmosis and preservatives known in the art.

Various modes of carrying out the invention are contemplated as being within the scope of the following claims particularly pointing out and distinctly claiming the subject matter which is regarded as the invention.

We claim:

1. A process for the recovery of milk coagulating enzymes from animal organs, comprising the steps of (a) mixing a polar solvent having a surface tension in the range of 18 to 72 dyne cm$^{-1}$ with finely divided animal organs, said organs constituting bovine abomasun, and (b) extracting the organ/polar solvent mixture in a salt solution at a pH in the range of 5.8 to 6.0 to provide an extract containing milk-coagulating enzymes, said salt being present in a concentration from about 2% to about 5% by weight and being water soluble and edible and capable of maintaining said pH in said range when used in said concentration.

2. A process according to claim 1, wherein the polar solvent is selected from the group consisting of ethanol, propylene glycol, glycenol, sorbitol and mixtures thereof.

3. A process according to claim 1, wherein the polar solvent is present in a concentration from between about 5% and about 15% by weight.

4. A process for the recovery of milk-coagulating enzymes from animal organs comprising: (a) mixing a polar solvent with animal organs consisting of bovine abomasun, (b) extracting the organ/polar solvent mixture in a salt solution at a pH in the range of about 5.8 and about 6.0, said salt being present in a concentration of about 2% to about 5% by weight, said salt being water soluble and edible and capable of maintaining the pH within said range when used in said concentration, (c) lowering the pH of the extract to a value between about 3.2 and 4.8, (d) adding a first soluble salt to the extract, said first salt being capable of reacting with mucin present in the organs at a pH of about 3.4 to form a soluble salt/mucin complex, (e) adding a second precipitating salt to the extract, said second salt being capable of reacting with the soluble salt/mucin complex to form a precipitate at a pH from between about 5.6 to about 6.0, and (f) separating the precipitate from the extract.

5. A process according to claim 4, wherein the polar solvent is selected from a group consisting of ethanol, propylene glycol, glycerol, sorbitol, acetone, acetamide, acrylonitrile, 1,3-butanediol, diethylether, 1,2-ethanediol, furan, isopropyl acetate, pyrrole, and mixtures thereof.

6. A process according to claim 5, wherein the polar solvent has a surface tension between 18 and about 72 dyne.cm$^{-1}$ and is present at a concentration from between about 5 and about 15% by weight.

7. A process according to claim 4, wherein the salt solution contains a salt selected from the group consisting of sodium chloride, sodium sulfate, and mixtures thereof.

8. A process according to claim 4, wherein said first salt is selected from the group consisting of aluminum sulfate, aluminum chloride, potassium aluminum sulfate, alum, and mixtures thereof.

9. A process according to claim 4, wherein said first salt is present in a concentration from between about 0.5% and about 1.0% by weight.

10. A process according to claim 4, wherein said second salt is an alkaline cation selected from the group consisting of phosphates, oxides, hydroxides, and mixtures thereof.

11. A process according to claim 10, wherein the ratio of said second salt to said first salt is from between about 1:1 and about 1.5:1.

12. A process according to claim 4, wherein the step of lowering the pH comprises adding hydrochloric acid to the extract.

* * * * *